United States Patent [19]

Syers

[11] Patent Number: 5,112,294

[45] Date of Patent: May 12, 1992

[54] METHOD AND SYSTEM FOR FACILITATING CHAMBER-TYPE MEDICAL PROCEDURES

[76] Inventor: Charles S. Syers, 325 Ascot Rd., Hillsborough, Calif. 94010

[21] Appl. No.: 613,336

[22] Filed: Nov. 15, 1990

[51] Int. Cl.⁵ ............................................. A61M 21/00
[52] U.S. Cl. ...................................... 600/27; 128/745
[58] Field of Search ................. 128/745, 746; 600/21, 600/26-28

[56] References Cited

U.S. PATENT DOCUMENTS

| | | | |
|---|---|---|---|
| 3,014,477 | 12/1961 | Carlin | 600/27 |
| 4,553,534 | 11/1985 | Steegler | 600/28 |
| 4,640,266 | 2/1987 | Levy | 600/27 |

FOREIGN PATENT DOCUMENTS 888601  9/1953  Fed. Rep. of Germany ........ 600/27

*Primary Examiner*—Max Hindenburg
*Attorney, Agent, or Firm*—Townsend and Townsend

[57] ABSTRACT

Medical patients who suffer from claustrophobia or other forms of fear or anxiety which make it difficult or impossible for them to undergo chamber-type analyses such as magnetic resonance imaging and CAT scanning, are prepared for such procedures by placing a readily removable shell over the patient's head and playing a recording with the shell in place. The interior of the shell approximates the visual appearance of the inside of the actual chamber which the patient will be subjected to during the medical procedure, and the recording contains the sounds the patient would be expected to encounter during the actual analysis. The shell and recording are used by the patient at will, and in the privacy of his or her own home, and this is done a sufficient number of times and for a sufficient duration to accustom the patient to the environment, all in preparation for the actual medical procedure. The invention is also applicable to biofeedback techniques by providing the subject with a feeling of protection and isolation.

14 Claims, 1 Drawing Sheet

METHOD AND SYSTEM FOR FACILITATING CHAMBER-TYPE MEDICAL PROCEDURES

This invention is in the field of medical devices, and particularly devices related to psychological conditions.

BACKGROUND AND SUMMARY OF THE INVENTION

Certain medical procedures involve the placement of a patient inside an enclosed chamber, particularly one whose walls are in fairly close proximity to the patient's body. Such procedures generally require the patient to lie motionless for an extended period of time. In addition, the patient is frequently subjected to sounds and noises made by the chamber or equipment associated with it. Examples of such procedures are various imaging and scanning procedures, such as magnetic resonance imaging, diagnostic ultrasound, and computerized axial tomography (CAT scanning).

Certain persons suffer from claustrophobia or other types of conditions or mental states which render them susceptible to fear or anxiety during such procedures. For such persons, these procedures can be a frightening experience. Indeed, many find themselves incapable of withstanding such procedures, and either do not schedule such procedures at all, or are unable to complete the procedure, requiring it to be terminated before sufficient data have been obtained.

Occurrences such as these are often a source of embarrassment to the patient. In addition, they present difficulties to diagnostic and analytical facilities where such procedures are performed. These facilities generally schedule these procedures on a closely timed consecutive basis. If a patient requires a procedure to be terminated before its completion and then restarted, the scheduling can be upset, and time is wasted if not lost entirely. The presence of technical and medical personnel is also needed, and the costs incurred by the facility will increase substantially if excessive time is needed for any one procedure.

Alternatively, the patient is placed under sedation or, in some cases, general anesthesia, before the procedure is performed. This requires preparation and the presence of a qualified specialist or anesthesiologist, plus recovery time, all of which add considerably to the expense and time needed for the procedure.

Also relevant to the present invention is the technique of biofeedback, or the conscious regulation of one's bodily functions. These are functions such as heartbeat or blood pressure which are otherwise, or generally thought to be, involuntary. The regulation of these functions by force of will requires intense relaxation and concentration on the part of the subject, and frequently the need to maintain silence and a motionless posture for extended periods. Difficulties encountered by those attempting biofeedback include a feeling of vulnerability and exposure to one's surroundings, and a sense of embarrassment in front of others present either intentionally or by chance. The result is a loss of the ability to concentrate, or disruptions in the continuity of the concentration and relaxation necessary to achieve effective biofeedback.

The present invention addresses these and related difficulties both in connection with chamber-type medical procedures and biofeedback by offering a means of shielding the subject to produce the psychological effect of isolation and encapsulation while exposing the subject to messages or sounds of a nature appropriate to the desired result.

In embodiments related to overcoming the fear and anxiety of enclosed spaces encountered in chamber-type medical procedures, the invention prepares a subject before going to a medical facility where the procedure is to take place. In this aspect, the invention is specifically directed to those persons who suffer from claustrophobia and other related fears and anxieties which interfere with or prevent their ability to undergo medical procedures of this type. In accordance with this aspect of the invention, the subject uses a device in the form of a small enclosure or shell designed to fit over at least the subject's head and optionally the subject's upper body or even the entire body, thereby giving the subject a mental impression similar to the experience of placing his or her head, if not entire body or substantial portion thereof, inside the actual chamber used in the medical procedure. The device is supplemented by a recording which mimics the sounds which the subject will hear when undergoing the actual procedure. Beyond these similarities to the actual chamber, the device will differ from the chamber in various ways, including the fact that it will be readily removable by the subject and will lack any of the actual equipment or functional features of the chamber.

In embodiments related to biofeedback inducement, the subject uses a similar small enclosure or shell, again designed to fit over at least the subject's head and optionally the subject's upper body or even the entire body, thereby giving the subject a mental impression of isolation, protection and security. The shell is preferably supplemented by a biofeedback recording, and the subject's susceptibility and response to the recording is enhanced by the use of the shell.

Other features, aspects and advantages of the invention will be apparent from the description which follows.

DETAILED DESCRIPTION OF THE INVENTION AND PREFERRED EMBODIMENTS

Figure 1:
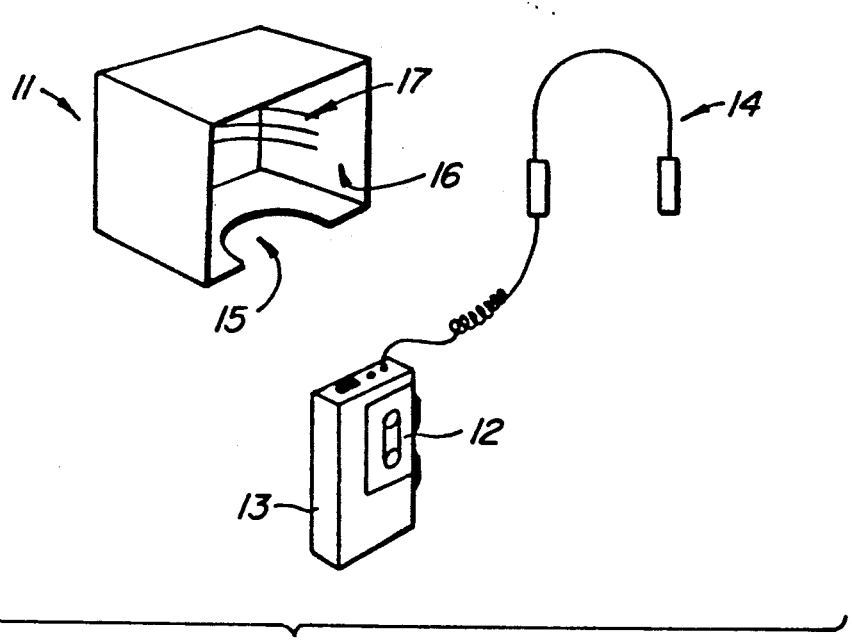
FIG. 1 is an illustration of the components of one example of a system in accordance with the invention.
Figure 2:
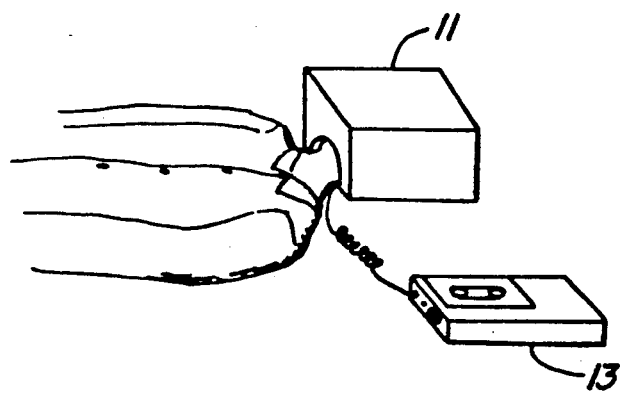
FIG. 2 depicts the system of FIG. 1 in use by an adult human preparing to undergo an actual medical procedure such as magnetic resonance imaging or a CAT scan.

The primary elements of the system and method of this invention are a head or body enclosure or shell which can be easily positioned and is readily removable by the person using it, and a sound recording which either induces relaxation and focusing on one's body, or approximates the sounds which the person will encounter during a chamber-type medical procedure. FIG. 1 depicts one example of a shell 11 as contemplated by the invention, and a sound recording in the form of a magnetic tape cassette 12 in a portable cassette player 13 fitted with earphones 14.

The shell 11 is an artificial enclosure. It may be constructed of any opaque material such as paper, cardboard, plastic, wood, or any other inexpensive, lightweight material. The sole purpose of the shell is to enclose the patient's head, leaving the patient with a visual impression of being enclosed inside a chamber like the one the patient will actually be enclosed in during the medical procedure. The shell need not encircle the patient's head entirely, but only to the extent that the patient's entire field of vision is covered. In the particular embodiment shown in FIG. 1, the shell is entirely open on one side, which is the side corresponding to the back of the patient's head. This is for purposes of convenience in positioning and removing the shell. This embodiment also includes a cutout 15 for the patient's neck. While the particular shell shown in the drawings covers only the patient's head, this is but one example of the general concept embodied in this invention. In variations of this structure, the shell may extend over the patient's shoulders or further down the patient's body. The only requirement is that the patient's field of vision is entirely covered, so that the patient is not capable of seeing outside the shell when it is in place.

For situations in which the invention is used as preparation for a chamber-type medical imaging procedure, it is a requirement of the shell that it be readily removable by the patient, since it is important that the patient be assured that he or she can remove the shell at any time when the patient feels his or her level of fear or anxiety rising. This is why the shell is preferably made of lightweight material which the patient can easily lift by hand. This is also an advantage in biofeedback applications of the invention for convenience in storage, handling and transport. For further convenience, the shell may also be of a collapsible construction in such a manner that it can be folded flat when not in use. This is readily accomplished by the appropriate placement of fold lines and hinge joints, as well as tabs and slots, support rods or similar structural elements or devices to hold the shell in the open position when desired. While none of these features are shown in the drawings, specific examples and methods of implementing and attaching them will be readily apparent to those skilled in the art.

For chamber-type procedure applications, the interior surface 16 of the shell will bear a pictorial representation 17 which approximates the appearance of the inside of the actual chamber used in the medical procedure that the patient is preparing for. The representation may be either a photograph or a drawing, indeed any form of depiction which will have the appearance of the actual shapes, colors and light intensity which the patient will see from the perspective which the patient's head will occupy during the procedure. The pictorial representation may be enhanced by an artificial light source included as part of the construction of the shell itself (the light source not being shown in the drawing). Alternatively, the shell may be designed to rely on light entering from the outside through the neck cutout 15 or around the edges of the open side of the shell. In most cases, the size and configuration of the shell, as well as the material which it is made from and the manner in which it is constructed will affect the choice of how the pictures on the interior wall of the shell will be made visible to the patient. As a further optional refinement, the pictorial representation on the shell interior may be done as a three-dimensional picture, which the patient will accordingly view with the appropriate eyeglasses if necessary. For biofeedback applications, the interior wall of the shell need not have a pictorial representation, but may instead be entirely black.

While the shell in the drawing is shown in a box-like configuration, other shapes are contemplated within the scope of the invention. Spherical and cylindrical shapes are examples.

The sound recording may assume any conventional form, including magnetic tape, laser disk, or phonograph record. Magnetic tapes are particularly convenient. A cassette player 13 as shown in the drawing has the advantage of portability and ease of use, and earphones 14 are also particularly useful, since they permit the user to conduct the procedure without attracting the attention of or disturbing others within earshot.

The sounds included in the recording will be those appropriate to the purpose of the use of the device. For applications involving preparation for a chamber-type medical procedure, the sounds will duplicate those which the subject will encounter during the procedure. This will vary from one medical procedure to the next. For magnetic resonance imaging machines, for example, the appropriate sound will be a low level humming and grinding noise. The sounds may be a recording of the instrument itself during an actual procedure, or they may be artificially produced or synthesized.

In certain embodiments of the invention, these sounds are supplemented with instructional material in the form of a human voice conveying information to the patient. This information may be psychological in nature, directed at coaching the subject into relaxation and soothing or overcoming any claustrophobic fears which the subject may have. Biofeedback recordings may be used, as well as relaxation recordings, or music with subliminal relaxation messages. Alternatively, the information may be educational in nature, describing the actual instrument, and the medical procedure, possibly including how it works and what it is measuring or detecting. As a further alternative, the recording may also include material of an entertainment nature, such as music, sports commentary, or a narrative of some kind, as a distraction to the patient. Regardless of the supplementary material, all such recordings will preferably include the background instrumental noise which the patient would be expected to hear during the medical procedure.

For biofeedback applications, the recording will be a biofeedback recording, with verbal and optionally subliminal messages designed to induce relaxation, concentration and focusing on one's bodily functions. Recordings which are already in the state of the art may be used.

Use of the system described herein by a subject can be done either in a supervised or unsupervised manner. One advantage of the system is that it can be conducted by the subject alone in the privacy of his or her own home. In most cases, the subject will place the device over his or her head and play the tape, and for situations where the subject is attempting to overcome claustrophobia, taking care to make sure that his or her eyes are open at all times. The shell will be held in place with the tape playing for initially a short period of time, and will be repeated as often as needed to accustom the subject to the experience. These exposure periods can be monotonically increasing in duration, to gradually extend the length of time that the patient can comfortably remain in the enclosed environment, and the rest periods separating them can likewise be monotonically decreasing. In any event, the subject can take as much time as possible and as many trials as possible to achieve a satisfactory degree of comfort with the sight and sound environment like that of the actual medical procedure.

As an option, the tape or other recording can be brought to the actual medical procedure by the subject, and played during the procedure, as a further means of reassuring and calming the subject. This will be particularly useful when the recorded material includes psychologically soothing or entertaining material.

This invention is applicable to any number and a wide variety of medical procedures which involve placement of the subject inside an enclosed chamber. This includes fully enclosing chambers as well as partially enclosing chambers, and generally extends to all chambers which cover most if not all of the patient's field of vision. Examples are CAT scanning equipment, magnetic resonance imaging equipment, and ultrasound equipment. Other types of equipment and procedures for which the present invention is appropriate will be readily apparent to clinical laboratories, medical technicians and doctors, and others skilled in the art.

The foregoing is offered primarily for purposes of illustration. It will be readily apparent to those skilled in the art that variations and modifications in terms of equipment, materials and procedures beyond those described herein may be made without departing from the spirit and scope of the invention.

What is claimed is:

1. A method of preparing a subject suffering from claustrophobia for a medical procedure which requires placement of at least the head of said subject inside a chamber, said method comprising:
   (a) placing over the head of said subject a shell readily removable by said subject, said shell having an interior surface bearing a pictorial representation approximating the appearance of the inside of said chamber; and
   (b) directing prerecorded sounds to the hearing of said subject with said shell so placed, said sounds approximating those to be encountered by said subject during said medical procedure.

2. A method in accordance with claim 1 in which steps (a) and (b) are conducted simultaneously for successive periods of time, said periods defined as exposure periods and separated by rest periods, the duration of each said exposure period selected to gradually accustom said subject to said shell and said prerecorded sounds without generating a claustrophobic reaction.

3. A method in accordance with claim 2 in which said exposure periods are monotonically increasing in duration.

4. A method in accordance with claim 1 in which step (b) further comprises directing prerecorded instructional material to the hearing of said subject simultaneously with said prerecorded sounds.

5. A method in accordance with claim 4 in which said instructional material is an educational description regarding the operation of said medical procedure.

6. A method in accordance with claim 4 in which said instructional material is coaching material designed to assist said subject in overcoming claustrophobic fears.

7. A method in accordance with claim 1 in which said medical procedure is magnetic resonance imaging, and said pictorial representation is a picture of the interior of a magnetic resonance imaging chamber.

8. A method in accordance with claim 1 in which said medical procedure is CAT scanning, and said pictorial representation is a picture of the interior of a CAT scan chamber.

9. A system for preparing a subject suffering from claustrophobia for a medical procedure which requires placement of at least the head of said subject inside a chamber, said system comprising:
   a shell sized to fit over the head of an adult human, said shell being one which is readily removable by an adult human over whose head said shell has been placed and which has an interior surface bearing a pictorial representation approximating the appearance of the inside of said chamber;
   a recording of sounds approximating those audible to one undergoing said medical procedure; and
   means for playing said recording to a subject over whose head said shell has been placed.

10. A system in accordance with claim 9 in which said recording further includes instructional material.

11. A system in accordance with claim 10 in which said instructional material is an educational description regarding the operation of said medical procedure.

12. A system in accordance with claim 10 in which said instructional material is coaching material designed to assist said subject in overcoming claustrophobic fears.

13. A system in accordance with claim 9 in which said medical procedure is magnetic resonance imaging, and said pictorial representation is a picture of the interior of a magnetic resonance imaging chamber.

14. A system in accordance with claim 9 in which said medical procedure is CAT scanning, and said pictorial representation is a picture of the interior of a CAT scan chamber.

* * * * *